United States Patent [19]

Savoyet

[11] Patent Number: 4,855,601

[45] Date of Patent: Aug. 8, 1989

[54] METHOD AND DEVICE FOR AUTOMATIC SPECTROMETRIC ANALYSIS OF A LIQUID, PARTICULARLY OF MILK

[75] Inventor: Jean-Louis Savoyet, La Motte d'Aveillans, France

[73] Assignee: Societe Civile de Brevets, J.L.S., La Motte d'Aveillans, France

[21] Appl. No.: 114,273

[22] Filed: Oct. 27, 1987

[30] Foreign Application Priority Data

Oct. 30, 1986 [FR] France ................. 86 15160

[51] Int. Cl.$^4$ ............................................. G01J 3/36
[52] U.S. Cl. ..................... 250/339; 250/359.1; 250/360.1; 250/341; 422/66; 436/23
[58] Field of Search ............... 250/339, 359.1, 360.1, 250/355.1, 340, 341, 304, 453.1, 454.1, 455.1; 436/23, 44, 155; 422/66

[56] References Cited

U.S. PATENT DOCUMENTS

| | | | |
|---|---|---|---|
| 3,260,413 | 7/1966 | Natelson | 422/66 |
| 3,368,872 | 2/1968 | Natelson | 436/44 |
| 3,734,622 | 5/1973 | Adler | 356/338 |
| 3,854,703 | 12/1974 | Gibbs et al. | 436/44 |
| 4,076,983 | 2/1978 | Hopkins et al. | 250/341 |
| 4,247,773 | 1/1981 | Nexo et al. | 250/339 |
| 4,257,862 | 3/1981 | Schnipelsky | 422/67 |
| 4,310,763 | 1/1982 | Shields | 250/339 |
| 4,415,809 | 11/1983 | Shields | 250/339 |
| 4,420,566 | 12/1983 | Jessop et al. | 250/339 |

FOREIGN PATENT DOCUMENTS

| | | | |
|---|---|---|---|
| 0122749 | 10/1984 | European Pat. Off. | 250/339 |
| 2153083 | 4/1973 | France . | |
| 2161618 | 7/1973 | France . | |
| 7201571 | 8/1973 | Netherlands . | |

Primary Examiner—Janice A. Howell
Assistant Examiner—William F. Rauchholz
Attorney, Agent, or Firm—Townsend & Townsend

[57] ABSTRACT

A method and device for automatic spectrometric analysis of a liquid, particularly of milk, is provided. A plate with an aperture is inserted into a cell containing the liquid. The plate is then withdrawn from the cell, leaving the aperture filled with a defined volume of the liquid. A jet of air is used to deposit the volume of liquid onto a plaque. The plaque is then moved into vertical alignment with the spreading device. The spreading device includes a bent wire rotatable by, for example, a motor for spreading the liquid into a circular spot. Preferably, the spot is dried while it is being spread. The plaque is then moved adjacent to a spectrometric analysis device for, for example, passing infrared radiation through the sample and to a detector, preferably configured to detect several wavelengths. The plaque carrying the sample is then moved to a cleaning station where it is cleaned by wiping the spot, preferably with a tape of filter paper wetted with detergent or solvent.

20 Claims, 5 Drawing Sheets

METHOD AND DEVICE FOR AUTOMATIC SPECTROMETRIC ANALYSIS OF A LIQUID, PARTICULARLY OF MILK

The invention relates to the analysis of a liquid, and more particularly of a liquid containing solid matter in suspension or in solution in a solvent, as is the case, for example, with milk, in order to determine the concentrations of the various constituents in the solvent, which is naturally water in the case of milk.

In order to perform this analysis, one of the most widely known methods is infrared spectrometry which employs spectrometers consisting essentially:

of a source of infrared radiation equipped with wavelength selection filters or with a monochromator device enabling a wide spectrum to be scanned, of at least one cell for enclosing the sample being analyzed, this cell particularly comprising two parallel walls through which the radiation passes, and of a sensor which makes it possible to detect the intensity of the radiation which has passed through the cell and through the thin specimen held between the two parallel walls, in order to determine the radiation attenuation produced by this sample.

The measurement is always comparative and employs either a spectrometer with two cells, one containing the pure solvent to serve as reference and the other the sample, the signal corresponding to the two cells being directed alternately onto the detector in a synchronous manner, or a single-cell spectrometer in which two infrared beams respectively corresponding to the wavelength for analysis of a constituent, which wavelength is strongly absorbed by this constituent, and to a reference wavelength which is absorbed by this constituent in a negligible manner, are directed alternately onto the detector through the same specimen, also in a synchronous manner.

In both cases, use is made of a number of characteristic wavelengths corresponding at least to each of the constituents being investigated, that is to say, in the case of milk, to fats, to proteins and to lactose.

This conventional analysis system has many disadvantages, the greatest of which is linked with the very low sample thickness, necessary in order to attenuate the signal passing through the cell as little as possible. As a result of this, the measurement cell is partly obstructed owing to the effect of sedimentation of the solid matter present in the solvent when a number of successive analyses are performed without the cell being cleaned. Furthermore, it is extremely difficult to ensure efficacious cleaning of these extremely closely placed inner faces of the cell, with the result that the unavoidable persistence of residual traces originating either from the previously analyzed material or from the cleaning liquid, makes it necessary to recalibrate the instrument frequently.

The problems of handling, of measurement, of cleaning and of recalibration, among others, make it absolutely necessary for known spectrometers to be used in the laboratory, and in practice prohibit their use in the field. This results in another disadvantage, which is the major delay which occurs between a sampling and the performing of the analysis, a delay which consequently falsifies this analysis when a changeable product such as milk is involved, in which the lactic acid produced by microbial degradation produces a considerable error in the measurement. Furthermore, an even longer delay occurs between any sampling and the knowledge of the result of analysis, and this is also a major disadvantage when this result is awaited for the purpose of controlling the herd. Ideally, therefore, it would be necessary to have the ability to perform this analysis in a rapid automatic manner and on site.

Another disadvantage of the conventional methods is the presence of the solvent, which virtually always constitutes the essential component in the composition of the liquid and which exhibits high absorption of the infrared radiation. This is particularly the case with water, the solvent in the case of milk, whose solids content is always relatively low compared with the water content. It is this phenomenon which in practice results in the thickness of the sample being limited to a few microns, leading to the problems described earlier. Another consequence of this is an inaccuracy in the measurements, where the absorption which is characteristic of the solid matter being analyzed represents only a low relative value compared with the absorption by the solvent.

The objective of the invention is to provide a method and a device for spectrometric analysis, which eliminate the previous disadvantages, especially the problems of handling, of delay and of inaccuracy, which are related to the cell and to the solvent, among other factors.

The method according to the invention consists:

in doing away with the cell by depositing a perfectly calibrated small volume of liquid on a plane and horizontal surface of a material which is transparent to the wavelengths employed, and then spreading the said calibrated volume in the form of a spot of well-determined, for example circular, surface area, with the aid of a spreading device, preferably rotary, which finally ensures a determined sample thickness, thereby enabling the infrared radiation to pass only through one solid wall, but, above all, permitting an easy and effective cleaning of this plane surface by wiping and polishing, in doing away with the solvent by drying this spot, this being possible precisely by virtue of the fact that the spot which is spread out offers a large surface area to free air, and also by virtue of the great ease of subsequent cleaning of the dried spot.

The device for making use of the method according to the invention essentially comprises a unit for producing a calibrated volume of liquid and depositing it on a sample-carrier, a rotary device for spreading the spot, preferably combined with drying it with hot air, a device for spectrometric analysis of the dried spot on the sample-carrier, a device for cleaning and wiping the spot, and lastly a mechanical means moving the sample-carrier automatically in order to cause it to occupy the various preceding stations successively in time, preferably in a rectilinear and horizontal motion. However, without departing from the method described, the use of a linear device could be replaced by that of a circular device which would produce a similar result.

Other special features of the invention will become apparent from the description which will follow of an embodiment taken by way of example and shown in the attached drawing, in which.

Figure 1:
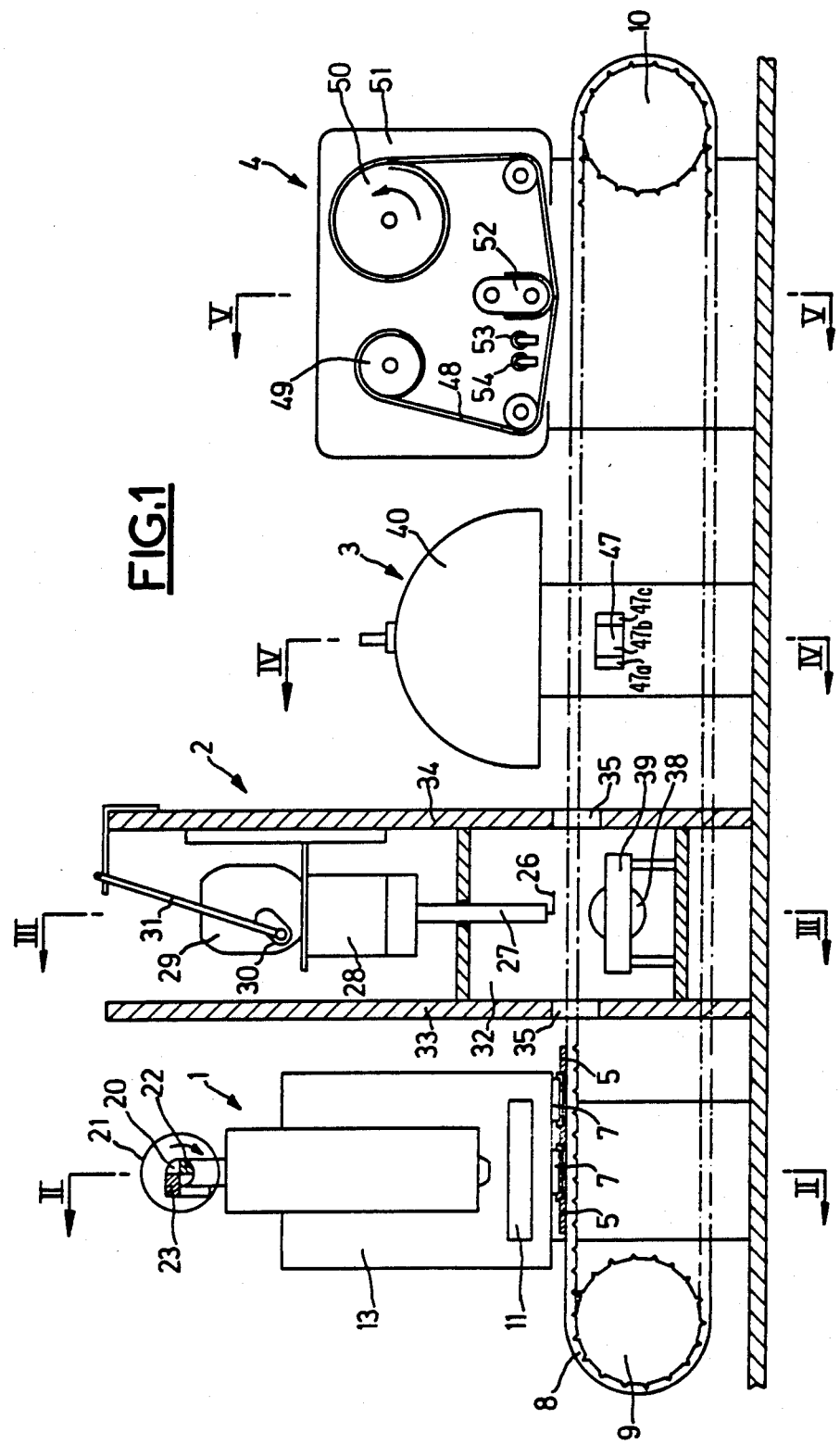
FIG. 1 is an elevation view with partial section of the whole device.

FIG. 1 shows the various stations 1, 2, 3 and 4, through which a single sample-carrier 5 travels in succession by virtue of a horizontal, preferably rectilinear, movement. This sample-carrier 5 is in the shape of a plaque sliding between two side guides 6, which can be seen in FIG. 2 and those which follow, and it carries one or preferably two small, parallel-faced plaques 7 made of a material which is transparent to the wavelengths employed. In particular, this material may be silicon or germanium.

Alternatively, the specimen-carrier may be followed by one or a number of others like it, permitting a shortening of the analysis time, that is to say that during one operation in the sequence, another may be taking place (e.g.: first sample-carrier analysis, a second sample-carrier spreading, drying, and the like).

Similarly, the number of tablets may be greater for each sequence in order to perform a double analysis permitting averaging, increase in accuracy, or detection of an error by comparison of the respective values obtained.

In the embodiment shown, the means for moving the specimen-carrier plaque 5 rectilinearly in its guides 6 is provided by a cog belt 8 to which it is secured and which is driven between two outermost pulleys 9 and 10, one of which is driven by a stepping motor, not shown. This motor is naturally capable of running in either direction and after each operation permits the specimen-carrier plaque 7 to be moved in the desired direction and precisely for the desired distance, in order to travel successively through the various stations 1, 2, 3 and 4 in the order shown, without it being necessary for this purpose for the four stations to be distributed uniformly in space in this same order.

Any other method of guidance can be envisaged (e.g.: a turntable controlled by a stepping motor or tachymetric device).

The first station 1 is a dispensing station the purpose of which is to withdraw a small but precise volume of the liquid to be analyzed and to deposit it on a small plaque 7. Any device for precise volumetric dispensing, which is independent of the surface tension of the liquid, which can vary, may be employed for this purpose. In the example chosen, this device consists of a sliding plaque 11, which can be seen especially in FIG. 2, this plaque, preferably made of ceramic, having parallel faces ground to a highly precise thickness dimension, while being pierced by at least one bore 12, also of a precise diameter, whose inner walls are coated with a nonwetting product such as polytetrafluoroethylene. Furthermore, this plaque 11 can slide in a leakproof manner between packings in order to enter through the wall 13 of a sample storage chamber in which the sample to be analyzed is delivered by a tube 14 and then removed after analysis by a tube 15. When the sampling device operates by means of a pressure reduction, an additional tube 16 may also be provided in the upper part, to produce the pressure reduction.

Figure 2:
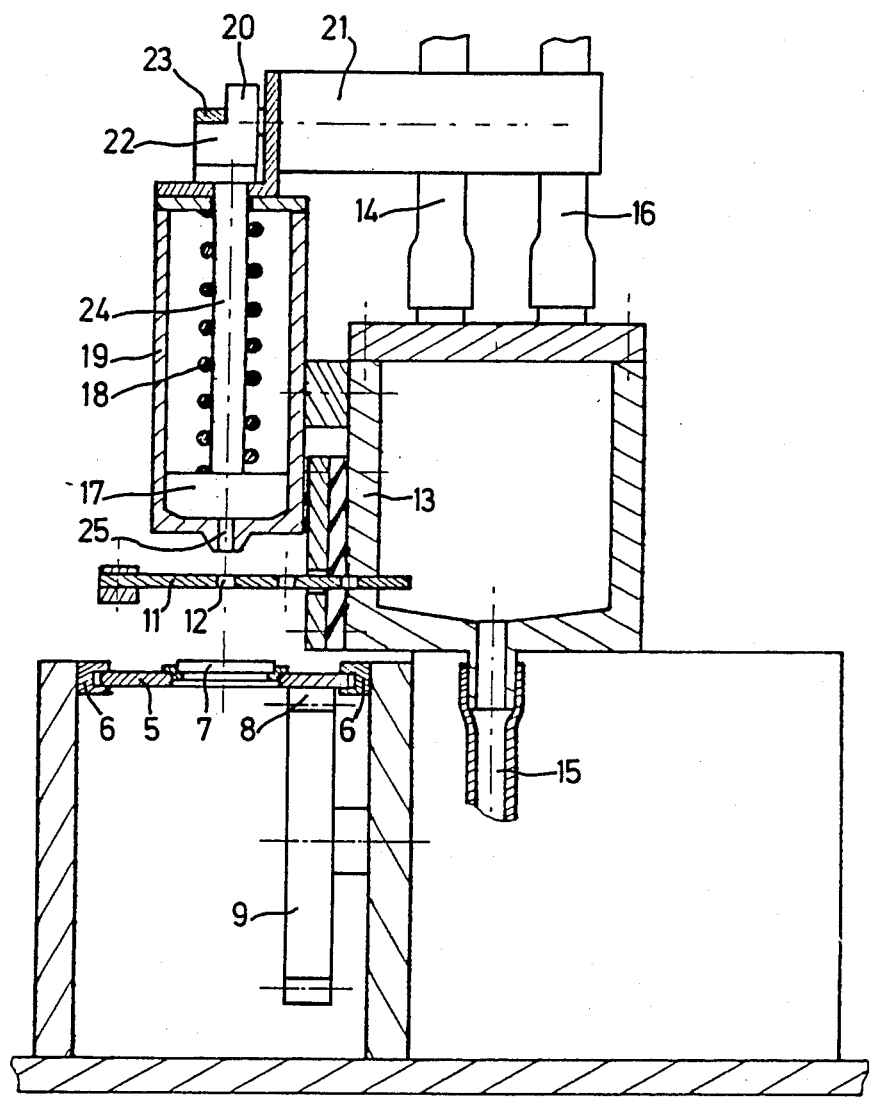
FIGS. 2, 3, 4 and 5 are vertical cross-sections along II-II, III-III, IV-IV and V-V of FIG. 1, respectively.
Figure 3:
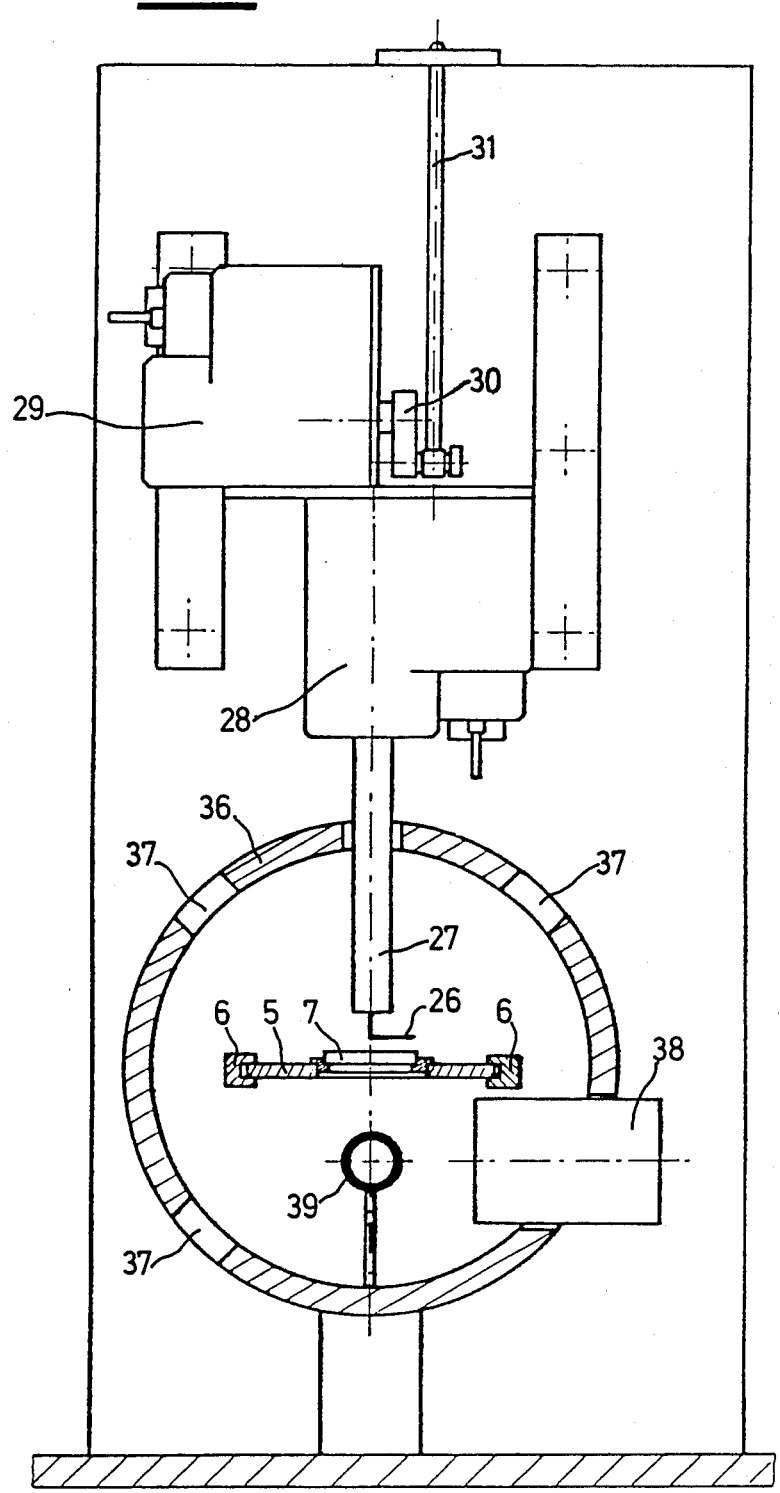
Figure 4:
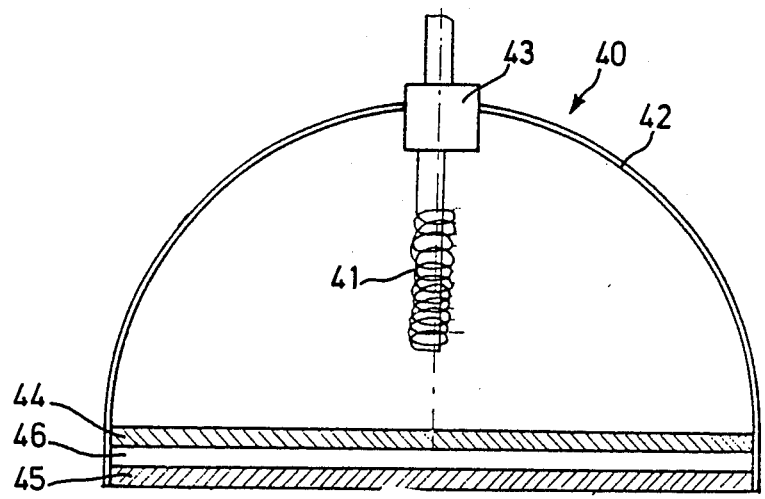

A reciprocating travel mechanism, not shown, produces the sliding of the plaque 11 between a completely inserted position, where its hole 12 is completely immersed in the liquid, and a completely withdrawn position where it is just vertically in line with a plaque 7 as shown in FIG. 2. In this position, the extremely precise cylindrical volume of this liquid which has thus been calibrated is generally held by capillarity, without, however, the capillary tension forces being capable of intervening in the determination of this volume, as would be the case, for example, with a medicine dropper.

In order to expel this volume and to make it fall onto the small plaque 7, a simple air jet is employed, which is produced in the example with the aid of a piston 17 loaded by a spring 18 and travelling in a cylinder 19, by virtue of a cam 20 driven by a motor 21. This cam 20 comprises a finger 22 capable of encountering and lifting a stub 23 forming an integral part of the rod 24 of the piston 17, in order to lift it while compressing the spring 18. When the finger 22 escapes sideways from the stub 23, the abrupt fall of the piston expels a small volume of air through the orifice 25 which blows along the axis of the hole 12 and thus expels the calibrated volume of liquid which falls onto the small plaque 7, forming a meniscus on the latter. Another means such as an air or gas generator may be employed.

The plaque 5 of the sample is then moved in order to be brought to the station 2, where spreading and drying are carried out. This spreading is produced by means of a rectangularly bent wire 26 made of tungsten or of a nonwetting product, this wire being carried by a spindle 27 in order to be driven in rotation by a motor 28, after having been lowered into contact with the small plaque 7 by a suitable mechanism consisting, for example, of a motor 29, a crank 30 and a connecting rod 31.

The rapid rotation of the rectangularly bent wire 26 in contact with the small plaque 7 produces the spreading of the precise volume of liquid deposited in the form of a circular spot of a highly accurate diameter and in a repetitive manner. Furthermore, it ensures an excellent homogenization of the product, by breaking up the large molecules of fatty matter together with an excellent dispersion.

The operation is preferably carried out inside the enclosure 32 of an oven consisting of parallel walls 33 and 34 fitted with windows 35 for the entry and the exit of the plaque 7, and a wall 36, for example cylindrical, equipped with orifices 37 for the circulation of air which is blown by a fan 38 over a resistance heater 39, preferably placed below the sample-carrier in order to heat the small plaque and air at the same time. Alternatively, any other means of heating could be employed, such as heating by infrared radiation. Furthermore, the oven heating is preferably thermostatic. This heating must be sufficient to rapidly dry the small volume of liquid spread on the circular surface area referred to, but at the same time insufficient to alter the product.

After drying and lifting the spindle 27 by means of the lifting device 29, 30, 31, the small plate 7, thus provided with a dry spot of the product to be analyzed, freed from its solvent and consequently representing only the dry matter present in the initial precise volume distributed onto the precise circular surface area referred to, is once again moved in order to be brought to the third station 3, where the spectrometric analysis as such is carried out, for example with the aid of a conventional instrument comprising a source of infrared radiation 40 and filters, or else a monochromator such as described in French Pat. No. 2,540,626, and, naturally, a radiation sensor 47.

By way of improvement, the invention provides for the use, as a source of infrared radiation 40, of a carbon filament 41 arranged in a hemispherical or parabolic wall 42 forming a reflector, of such shape that it ensures excellent focusing in the case in question and covers the greatest part of the surface of the dry extract and received in its totality by the sensor or sensors, preferably with a Peltier device 43 responsible for cooling this reflector. The lower face of the reflector 42 is closed by a disc 44 made of a material transparent to infrared, for example of silicon, and preferably also by a second similar disc 45 separated from that preceding by a total or partial vacuum 46, this being in order to prevent interfering infrared re-emissons. Vacuum is also produced in the enclosure.

The detector 47 of a suitable type is placed below the level of the sample-carrier 5. Use may be made, in particular, of a substrate on which one or more photo-transistors are produced or fastened, each sensitive to a well-determined frequency band, or each covered with a suitable filter allowing the desired band to pass through as shown by 47a, 47b, and 47c in FIG. 1. This arrangement enables measurements to be performed simultaneously for the various bands, or at least rotation of the filters or of the monochromator to be avoided, the principle of the invention remaining applicable even in the case where the filters rotate.

More particularly in the case of milk, the bands to be employed are preferably the following:

(a) the band from 2990 to 2880 waves/cm, i.e. from 3.355 to 3.472 μm;
(b) the band from 1770 to 1720 waves/cm, i.e. from 5.650 to 5.814 μm;
(c) the band from 1580 to 1490 waves/cm, i.e. from 6.329 to 6.711 μm; and
(d) the band from 1070 to 1000 waves/cm, i.e. from 9.345 to 10 μm.

Band (a), which is that most widely employed, is sensitive to the fatty matter of milk, but also partly sensitive to proteins. On the other hand, band (b) is sensitive to the fatty matter content and practically insensitive to proteins and to lactose, with the result that it will be employed for preference. Bands (c) and (d) are sensitive to protein and lactose contents respectively. The four bands indicated, or at least the last three, will therefore be employed.

As in the case of cell systems, an additional wavelength band may be employed which is practically not absorbed by the products to be analyzed and which serves as reference for the measurement, or else, analogously to the device with two cells, a second small plaque 7 may be employed, which receives no liquid and which serves for comparison when using the characteristic radiations indicated, this method also making it possible to reveal the state of aging or other alteration (oxidation, and the like) resulting from the use:

(a) of the source,
(b) of the small plaque collecting the milk, this being done by comparing the signal level between the small reference plaque and the others.

The comparison of the various radiation intensities sensed in this manner by the detector 47 makes it possible, as a result, to determine the required contents with a high precision, because of the absence of a cell, the absence of water, of the precise comparative measurement and, lastly, of the great ease of cleaning of the upper surface of the small plaque(s) 7 before any measurement.

Figure 5:
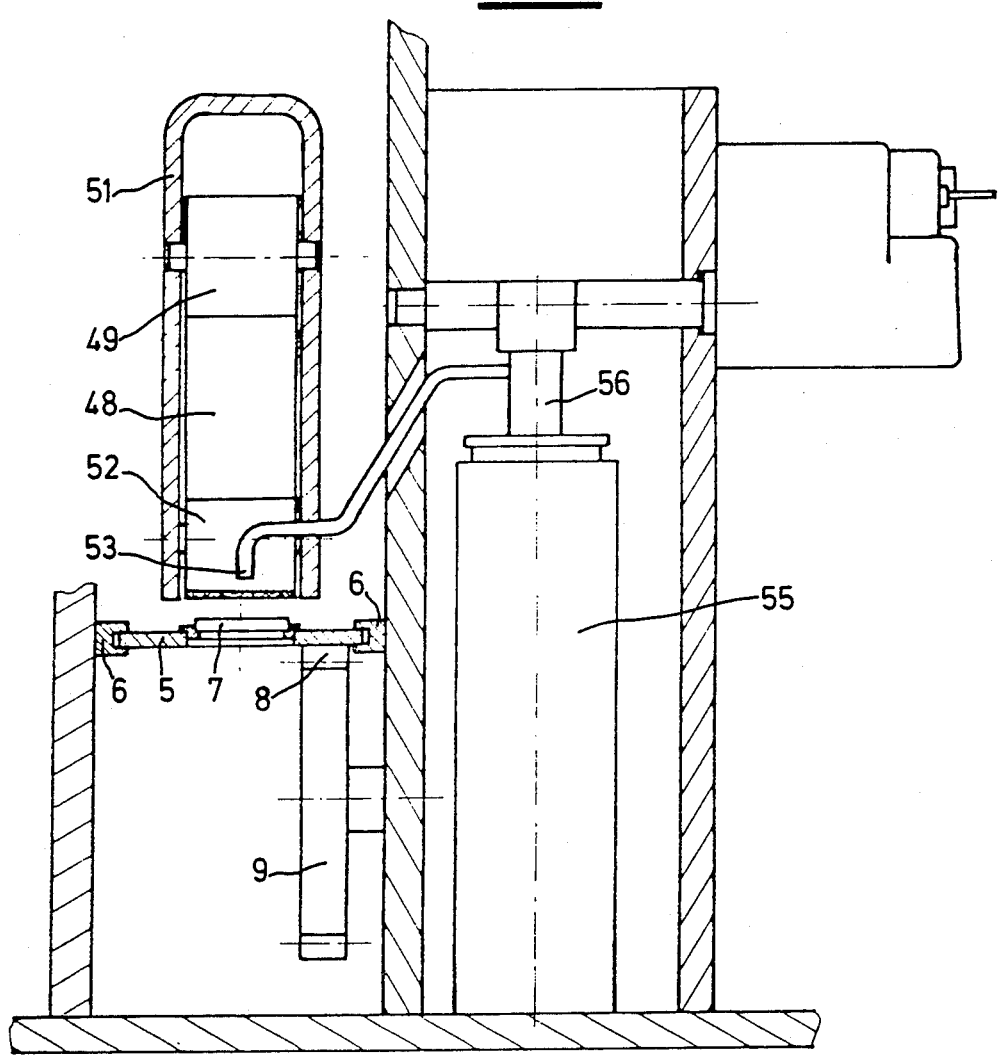

This cleaning is performed automaticaly at station 4 with the aid of a tape of filter-paper 48 mounted between a dispensing reel 49 and a receiving reel 50 of a cassette 51, with a press-pad 52 pushing this tape onto the top of a small plaque in the course of cleaning, two nozzles 53 and 54 being additionally provided for distributing a detergent liquid and a rinsing material from appropriate storage vessels such as 55 in FIG. 5 and with the aid of an injection device 56 driven by a suitable motor.

In order to ensure this cleaning, the movement of the small plaque is therefore produced by the stepping motor indicated above until the small plaque 7 is brought under the presser 52, under a region of the filter-paper 48 which has been wetted beforehand with detergent by the nozzle 53. After the presser 52 is lowered, the same stepping motor produces a lengthwise reciprocating motion of the specimen-carrier to produce the relative horizontal movement ensuring the surface cleaning of the small plaque. After dispensing of the rinsing material by the nozzle 54 and the forward movement of a suitable length of filter-paper 48, rinsing of the small plaque 7 is produced in the same manner, followed, lastly, by wiping with the aid of a dry zone of filter-paper. A similar effect is produced (cleaning) if the paper tape is driven in an alternating motion, it being possible to employ a combination of the two possibilities.

The second small plaque 7 used for comparison does not have to be cleaned in each cycle, but may naturally be so cleaned automatically in the same manner whenever needed.

The apparatus according to the invention can thus operate in a precise, certain and absolutely automatic manner, without requiring any tricky manipulation or any recalibration. Furthermore, it can easily be produced in a compact and portable form enabling it to be employed on site, especially where the milking is carried out, with all the advantages envisaged above, resulting from the absence of alteration in the product and to produce quick results facilitating the control of the herd.

In the examples described, the main product presented as being capable of forming the subject of the analysis is milk. In order to analyze certain milks containing very high concentrations (e.g.: buffalo cow milk with 130 g of fat/kilogram), the calibrated volume required for good spreading may be reduced and demineralized water may be added to it.

This produces a dilution which does not diminish the measurement in any way, bearing in mind the drying operation, with the water being used only for better spreading in the case under discussion.

It should be, stressed that there is no need for producing a highly accurate calibrated volume of the water added.

Following the same idea, various substances which are soluble or which have been made soluble by various means such as heating, preliminary comminution, and the like, can, in a first step, be dissolved or intimately combined in a solvent or binder medium; water, in the above case. Without its presence ever modifying the main product other than in a known and usable manner, the solvent or binder extracrs the main product, it being possible for the latter to be initially in various states: powder, paste, liquid (e.g.: all kinds of cheese, fish meal, and the like), with the means described being capable of utilization in order to determine the required concentrations, and with the infra-red wavelength range employed varying as a function of the nature of the product being investigated.

I claim:

1. Method of spectrometric analysis of a liquid, by measurement of the absorption in various frequency bands of an infrared radiation, characterized in that the following operations are carried out in succession:

a small volume of the liquid to be analyzed is accurately dispensed and is deposited on the planar upper surface of a small plaque (7) of a material which is transparent to the radiation employed.

this volume of liquid is spread on the small plaque over a well-defined surface area with the aid of a rotary device, the liquid spot thus produced is dried, until a dry spot is obtained, the small plaque (7) carrying its dry spot is subjected to spectrometic analysis in the absence of the solvent of the liquid, and the upper surface of the small plaque is cleaned by wiping and polishing before the next measurement.

2. A method, as claimed in claim 1, wherein said method of spectrometric analysis of a liquid comprises spectrometric analysis of milk.

3. A method, as claimed in claim 1, wherein said spreading of a volume of liquid over a well-defined surface area comprises spreading a volume of liquid over a circular surface area.

4. A method, as claimed in claim 1, wherein:
the step wherein said liquid spot is dried, is conducted at the same time as the step wherein said liquid is spread.

5. A method, as claimed in claim 1, wherein said step of automatically dispensing and depositing comprises:
providing a sliding plaque having a orifice and a non-wettable wall;
sliding said sliding plaque in a leakproof manner into a cell containing the liquid to be analyzed, wherein said orifice may be immersed in said liquid; and
sliding said sliding plaque outward through said wall of said cell to extract a cylindrical volume of liquid.

6. A method, as claimed in claim 1, wherein said depositing of a small volume comprises blowing a jet of air on said small volume to move said small volume onto said small plaque.

7. A method, as claimed in claim 1, wherein said spreading of said volume comprises:
providing a bent wire mounted at the end of a rotary spindle;
placing at least a portion of said bent wire in contact with said volume of liquid; and
rotating said rotary spindle to rotate said bent wire.

8. A method, as claimed in claim 1, wherein said cleaning of small plaque comprises:
contacting at least a portion of said small plaque with a tape; and
wiping said small plaque with said tape.

9. A method, as claimed in claim 8, further comprising wetting at least a portion of said tape with a material selected from the group consisting of detergents and solvents.

10. A device for spectrometric analysis of a liquid comprising:
first means for dispensing of a precise volume of liquid and depositing said volume liquid on a small plaque (7),
second means for spreading of this volume over a determined surface area to allow said liquid to dry into a spot,
third means for spectrometric analysis of the small plaque (7) carrying its dry spot, and
a device for wiping with the aid of a filter-paper tape (48) with suitable detergents and solvents, a device for producing movement (8, 9, 10), ensuring the movement of a small support-plaque (5) carrying at least one small plaque (7) to cause it to occupy the various stations in succession.

11. A device according to claim 10, characterized in that the means for dispensing the small precise volume of liquid consists of a sliding plaque (11) provided with an orifice (12) with a nonwettable wall and sliding in a leakproof manner through the wall of a cell (13) containing the liquid to be analyzed, so that the orifice may be immersed in the liquid in order to extract the precise cylindrical volume of liquid out of said cell and above the small plaque (7), this volume being purged onto this small plaque by a brief jet of air.

12. A device according to claim 11, characterized in that the said sliding plaque (11) is made of ceramic and that the orifice (12) is coated internally with a nonwetting product.

13. Device according to claim 1, characterized in that the spreading means consists of a rectangularly bent wire (26) mounted at the end of a rotary spindle (27) equipped with a means for approaching and withdrawing (29, 30, 31) for coming into contact with the small plaque (7), the whole unit being contained in an enclosure (32) fitted with a means of heating (39) and of ventilation (38).

14. A device according to claim 10, characterized in that a source of infrared radiation (40) is provided which consists of a carbon filament (41) contained in a reflector (42) equipped with a Peltier cooler (43) and is closed by two discs (44, 45) separated by vacuum and made of a material which is transparent to the infrared.

15. A device according to claim 10, characterized in that a radiation detector (47) is provided made up of a network of individual detectors mounted on the same substrate and each detecting one of the frequency bands employed for the spectrometric analysis.

16. Device according to claim 10, characterized in that the frequency bands employed for the spectrometric analysis comprise at least the following three bands:
1770 to 1720 waves/cm (5.650 to 5.814 $\mu$m),
1580 to 1490 waves/cm (6.329 to 6.711 $\mu$m), and
1070 to 1000 waves/cm (9.345 to 10 $\mu$m).

17. A device, as claimed in claim 10, wherein said device for producing movement comprises a device for producing horizontal rectilinear movement.

18. A device according to claim 17, characterized in that the relative horizontal movement ensuring the actions of cleaning by wiping and polishing of the small plaque (7) at the cleaning station, is produced by the same device responsible for the movement of the small sample-carrier plaque (5) to the various stations, by virtue of an alternation of the two directions of travel.

19. Device according to claim 10, characterized in that the filter-paper tape (48) used for the cleaning is loaded with the aid of a cassette (51) containing both a dispensing (49) reel and a receiving (50) reel.

20. A device, as claimed in claim 10, further comprising means for drying said volume spread over a determined surface area.

* * * * *